United States Patent
Lai

(10) Patent No.: US 6,596,733 B2
(45) Date of Patent: *Jul. 22, 2003

(54) USE OF NITRIC OXIDE SCAVENGERS TO TREAT SIDE EFFECTS CAUSED BY THERAPEUTIC ADMINISTRATION OF SOURCES OF NITRIC OXIDE

(75) Inventor: Ching-San Lai, Encinitas, CA (US)

(73) Assignee: Medinox, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/912,757

(22) Filed: Jul. 24, 2001

(65) Prior Publication Data

US 2001/0056108 A1 Dec. 27, 2001

Related U.S. Application Data

(62) Division of application No. 09/103,640, filed on Jun. 23, 1998, now Pat. No. 6,265,420.

(51) Int. Cl.⁷ .................. A61K 31/295; A61K 31/47; A61K 3/28; A61K 31/30
(52) U.S. Cl. ............... 514/310; 514/492; 514/499; 514/501; 514/502
(58) Field of Search ................. 514/310, 492, 514/499, 501, 502

(56) References Cited

U.S. PATENT DOCUMENTS 6,265,420 B1 * 7/2001 Lai ..................... 514/310

\* cited by examiner

*Primary Examiner*—Theodore J. Criares
*Assistant Examiner*—Jennifer Kim
(74) *Attorney, Agent, or Firm*—Stephen E. Reiter; Foley & Lardner

(57) ABSTRACT

Nitric oxide scavengers, such as dithiocarbamate-containing compounds, are used to reduce side effects caused by therapeutic administration of nitric oxide sources by administering the nitric oxide scavenger(s) to the subject after the therapeutic effect of the nitric oxide source has been achieved. For example, the nitric oxide source can be coadministered with the nitric oxide scavenger, with the latter formulated in a time release vehicle selected to delay release of the scavenger for a period of time sufficient to ensure that the therapeutic goal of the nitric oxide source has been achieved before release of the scavenger. Formulations and kits, including a bubble pack with pairwise arrangement of unit doses of a desired nitric oxide source and nitric oxide scavenger, are also provided. The side effects of sildenafil citrate (Viagra®), or of simultaneous administration of such a nitric oxide source in combination with another, such as nitroglycerin, are effectively controlled by the methods, formulations and kits of the invention.

13 Claims, 1 Drawing Sheet

Time (day)

USE OF NITRIC OXIDE SCAVENGERS TO TREAT SIDE EFFECTS CAUSED BY THERAPEUTIC ADMINISTRATION OF SOURCES OF NITRIC OXIDE

This Application is a Division of Ser. No. 09/103,640 filed Jun. 23, 1998 now U.S. Pat. No. 6,265,420.

RELATED APPLICATIONS

This application is related to pending U.S. patent application Ser. No. 08/863,059, filed May 23, 1997, which is a continuation-in-part application of pending U.S. patent application Ser. No. 08/767,125, filed Dec. 9, 1996, and to U.S. patent application Ser. No. 08/554,196, filed Nov. 6, 1995, now issued as U.S. Pat. No. 5,741,815, which is a continuation-in-part of U.S. patent application Ser. No. 08/459,518, filed Jun. 2, 1995, now issued as U.S. Pat. No. 5,756,540. This application is further related to pending U.S. patent application Ser. No. 08/884,600, filed Jun. 27, 1997, which is a continuation-in-part-application of U.S. patent application Ser. No. 08/561,594, filed Nov. 21, 1995, now issued as U.S. Pat. No. 5,757,532. This application is further related to pending U.S. patent application Ser. No. 08/899,087, filed Jul. 23, 1997, which is a continuation-in-part-application of provisional U.S. Patent Application Ser. No. 60/025,876, filed Sep. 10, 1996, now abandoned, and to pending PCT application WO 995160 filed Aug. 28, 1997. This application is further related to pending U.S. patent application Ser. No. 08/869,158, filed Jun. 4, 1997.

FIELD OF THE INVENTION

The present invention relates to therapeutic compositions and their use in treatment of disease states. More particularly, the present invention relates to methods and compositions for reducing side effects caused by administration to a subject of nitric oxide sources.

BACKGROUND OF THE INVENTION

As recently as 10 years go, nitric oxide was considered only a noxious gas that appeared in the exhaust of cars and in city smog, caused acid rain, and destroyed the ozone layer. This view changed tremendously in 1987 when nitric oxide was discovered to be produced in humans (Palmer, et al., *Nature*, 327:524–526, 1987; and Ignarro, L. J. et al., *Proc. Natl. Acad. Sci.*, 84:9265–9269, 1987).The status of nitric oxide was thus expanded from being an environmental threat to being a new pharmaceutical target of major medical importance (Carter, B. et al., *Anaesth Intensive Care*, 26(1):67–69, 1988; Moncada, S., *Methods Find Exp. Clin Pharmicol*, 19 Suppl A: 3–5, 1997; Vallace, P. and Moncada, S., *J. Royal College Physicians*, London 28: 209–219, 1994; and Romero, R., *Hum Reprod.* 13:248–250, 1998).

Nitric oxide is produced in the body by three different isoforms of the nitric oxide synthase (NOS) enzyme (see, for example, Singh, S. and Evans, T. W., *Eur. Respir. J.*, 10:699–707, 1997). Neuronal NOS (nNOS) is found in neurons and plays a role in memory and pain perception. Endothelial NOS (eNOS) is found in vascular endothelial cells and plays an active role in vasodilatation and blood pressure regulation. Inducible NOS (iNOS) is expressed in astrocytes, microglial cells, neutrophils and in many other tissues in response to stimulation by inflammatory cytokines.

Like other biomediators, the level of nitric oxide in the body is tightly regulated. Both overproduction and underproduction of nitric oxide are associated with many diseases and conditions (see, for example, Moncada, S. and Higgs, E. A., *FASEB J.*, 9:1319–1330, 1995). For example, excessive nitric oxide production is linked to many inflammatory diseases, including septic shock, hemorrhagic shock, allograft rejection, diabetes, arthritis, and neurogenerative diseases (Wolkow, P. P., *Inflamm. Res.* 47:152–166, 1998; Hierholzer, C. et al., *J. Exp. Med*, 187:917–928, 1998; Silkoff, P. E. et al., *Am. J. Respir. Crit. Care Med.*, 157:1822–1828, 1988; Pieper, G. M., *Hypertension*, 31:1047–1060, 1998; Stichtenoth, D. O., *Br. J. Rheumatol*, 37:246–257, 1998; and Molina, J. A. et al., *Drugs Aging*, 12:251–259, 1998). On the other hand, insufficient nitric oxide production has been associated with human diseases, including impotence, atherosclerosis, essential hypertension, pre-ecalmpsia, and congestive heart failure (Hass, C. A. et al., *Urology*, 51:516–522, 1998; McHugh, J. et al., *Am. J. Crit. Care*, 7:131–140, 1998; Cardillo, C. et al., *Circulation*, 97:851–856, 1998; Buhimschi, I. A. et al., *Hum. Reprod. Update*, 4:25–42, 1998; Abassi, Z. et al., *Am. J. Physiol.*, 274 (4 pt. 2):F766–F774, 1998).

A number of nitric oxide-releasing agents have been used to treat cardiovascular and pulmonary diseases associated with insufficient nitric oxide production (see, for example, Loskove, J. A. et al., *Am. Heart J.*, 129:604–13, 1995). For example, organic nitrates, such as nitroglycerin and isosorbide dinitrates, have been widely used in the treatment of vascular heart diseases, such as the prevention of angina (see, for example, Torfgard, K. E. and Ahlner, J., *Cardiovascular Drugs and Therapy*, 8:701–717, 1994). However, such therapeutically administered nitric oxide-releasing agents can cause deleterious effects, many of which result from elevated levels of nitric oxide, when combined with one another or when combined with therapeutic compounds that interfere with metabolism of nitric oxide in the body.

Nitric oxide is a potent vasodilator (see, for example, Palmer in *Arch. Surg.* 128:396–401 (1993) and Radomski & Moncada in *Thromb. Haemos.* 70:36–41 (1993). For example, in blood, nitric oxide produced by the endothelium diffuses isotropically in all directions into adjacent tissues. As nitric oxide diffuses into the vascular smooth muscle, it binds to guanylate cyclase enzyme, which catalyzes the production of cGMP, inducing vasodilation (see, for example, Ignarro, L. J., *Ann. Rev. Toxicol.* 30:535–560 (1990); Moncada, S., *Acta Physiol. Scand* 145:201–227 (1992); and Lowenstein and Snyder, *Cell* 70:705–707 (1992)). The overproduction of nitric oxide causes an extreme drop in blood pressure, resulting in insufficient tissue perfusion and organ failure.

Recently, patients taking sildenafil citrate (Viagra®, Pfizer Laboratories) for treatment of male impotence have experienced side effects, such as headache, hypertension and dyspepsia, particularly when the drug is used in conjunction with organic nitrate drugs (see, for example, Goldstein, I. et al., *N. Engl. J. Med.*, 338:1397–1404, 1998). Fatalities have been reported when Viagra® was used together with nitrate drugs, such as nitroglycerin.

There are additional situations in which a therapeutically administered source of nitric oxide can result in undesirable side effects. For example, the transfer of the gene encoding endothelial NOS into injured blood vessels reduces myointimal hyperplasia, as in restenosis, by providing a source of nitric oxide (see, for example, Janssens, S. et al., *Circulation*, 97:1274–1281, 1998). However, the continuing production of excessive nitric oxide from the NOS gene in the vessels can lead to nitric oxide-related oxidative damage in vivo.

Although therapeutically administered nitric oxide sources are beneficial in achieving therapeutic goals, such compounds can, in some cases, increase the level of nitric oxide above physiologically compatible levels in the subjects to whom they are administered. In other cases, the increased level of nitric oxide needed to achieve the increased level of nitric oxide may linger in the body longer than is therapeutically required. In addition, some subjects are treated with combinations of nitric oxide sources that may be administered separately to treat different conditions, but which, in combination, have an additive, or even synergistic, effect. In such cases, the patient may be unaware when a physiologically incompatible level of nitric oxide has been reached or when an otherwise therapeutic amount of a nitric oxide source becomes potentially dangerous due to combined effects of separately administered drugs.

It is known to use nitric oxide scavengers therapeutically to remove nitric oxide from the blood and/or tissues of subjects suffering from toxic levels of nitric oxide, such as those generated in many disease states (see, for example, Lai, C. S., U.S. Pat. Nos. 5,741,815; 5,756,540 and 5,757,532). Nitric oxide scavengers bind nitric oxide in vivo and the resulting complexes render nitric oxide harmless. The resulting complexes are eventually excreted in the urine of the host. Thus, nitric oxide scavengers are used to lower the level of nitric oxide in the subject, for example to a physiologically acceptable level.

However, new and better solutions are needed for the problem of controlling nitric oxide levels in subjects therapeutically administered sources of nitric oxide in treatment of disease states associated with depressed levels of endogenously produced nitric oxide. In particular, methods and compositions useful for administering nitric oxide scavengers to such subjects without compromising the therapeutic effect of the administered nitric oxide source are needed.

SUMMARY

In accordance with the present invention, there are provided methods for reducing side effects induced by therapeutic administration of a nitric oxide source, such as a nitric oxide-containing gas, a nitric oxide donor, a nitric oxide enhancer, a nitric oxide generator, and combinations thereof. The invention methods comprise administering to a subject in need thereof an effective amount of a physiologically compatible nitric oxide scavenger, such as a dithiocarbamate (or compound that releases a nitric oxide scavenger when activated, such as a disulfide derivative of a dithiocarbamate), so that the nitric oxide scavenger takes effect a sufficient amount of time after administration of the nitric oxide source to allow the desired therapeutic effect of the nitric oxide source to be achieved. Accordingly, administration of the nitric oxide scavenger can be delayed a sufficient amount of time after administration of the nitric oxide source for the therapeutic effect of the nitric oxide source to be achieved. Alternatively, the nitric oxide scavenger can be coadministered with the nitric oxide source, but contained within a time release vehicle that delays delivery of a substantial amount of the scavenger until the therapeutic effect of the nitric oxide source has been achieved.

In another aspect, the invention provides a formulation comprising an effective amount of a biologically compatible nitric oxide source and an effective amount of a physiologically compatible nitric oxide scavenger, or compound that releases a scavenger when activated, in a time release delivery vehicle that substantially delays release of the scavenger for a sufficient amount of time after administration of the formulation to a subject in need thereof that the nitric oxide source achieves a beneficial effect prior to the release of the scavenger.

In another aspect, the invention provides a kit comprising a unit dose of a nitric oxide source in a pharmaceutically acceptable carrier therefor, and a unit dose of a physiologically compatible nitric oxide scavenger in a pharmaceutically acceptable carrier therefor, optionally contained within a time release vehicle. The nitric oxide scavenger is optionally in a time release delivery vehicle to delay release of the scavenger until the therapeutic effect of the nitric oxide source has been achieved. The kit can advantageously be in the form of a bubble pack with the nitric oxide source and the nitric oxide scavenger arranged pairwise therein for ease of administration.

DETAILED DESCRIPTION OF THE INVENTION

Figure 1A:
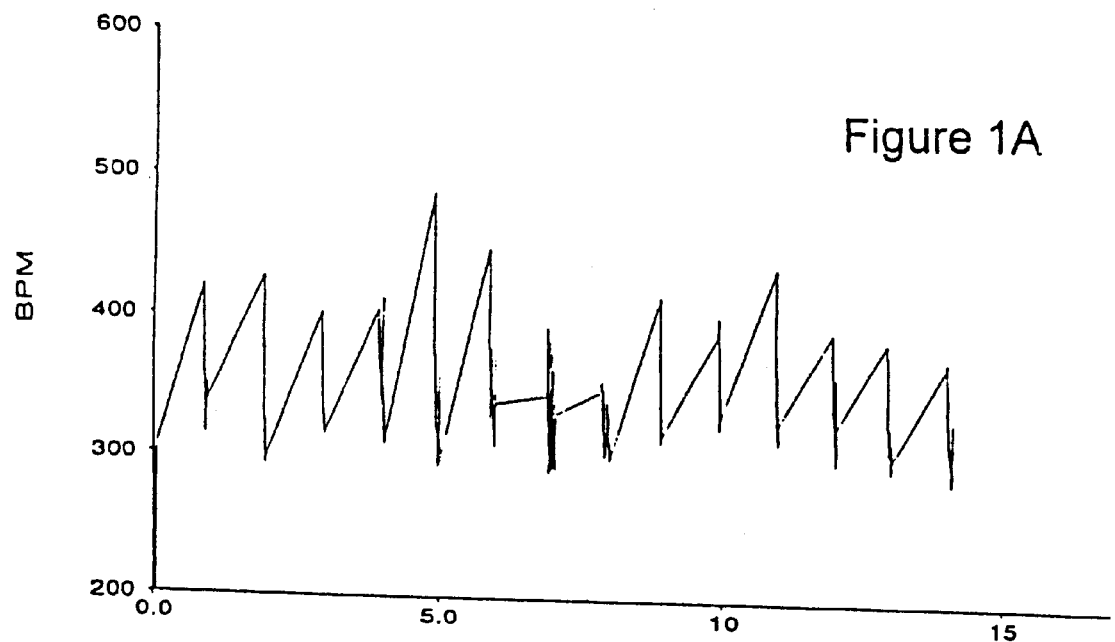
FIG. 1A is a graph showing the heart rate (beats per minute=BPM) of rats orally administered 10 mg/ml of L-proline dithiocarbamate in drinking water over a time course of 14 days.

In accordance with the present invention, there are provided therapeutic methods for reducing side effects induced in a subject by therapeutic administration of a nitric oxide source. The side effects induced by nitric oxide sources range from mild discomfort, such as dyspepsia, to death, in subjects with severely compromised cardiovascular systems, especially those administered more than one nitric oxide source.

In one aspect, the invention method comprises administering an effective amount of a physiologically compatible nitric oxide scavenger to a subject wherein the nitric oxide scavenger is administered so as to take effect a sufficient amount of time after therapeutic administration of a nitric oxide source to allow the desired therapeutic effect of the nitric oxide source to be achieved.

In another aspect, the invention provides methods for treating the effects of an elevated level of nitric oxide caused by therapeutic administration of one or more nitric oxide sources to a subject in need thereof by administering to the subject an effective amount of a physiologically compatible nitric oxide scavenger so as to lower the subject's level of nitric oxide to a physiologically compatible level.

Therapeutic nitric oxide sources whose undesirable side effects can be reduced in the practice of the invention method include nitric oxide containing gases, nitric oxide donors, nitric oxide enhancers, nitric oxide generators, and combinations of any two or more thereof. Although therapeutically administered nitric oxide sources are beneficial in achieving therapeutic goals, one of the potential side effects in subjects administered nitric oxide source(s) for therapeutic purpose is an excessive increase in the level of nitric oxide. These effects may linger in the body longer than is needed to achieve the desired therapeutic effect. In addition, when subjects are treated with combinations of nitric oxide sources that may be administered separately to treat different conditions, but which, in combination, have an additive, or even synergistic, effect on nitric oxide levels in blood, nitric oxide levels may rise above the range that is physiologically compatible.

The nitric oxide scavengers used in the invention method chemically bind free nitric oxide in the blood stream and tissues and are administered in sufficient amount to lower the level of nitric oxide in the subject to a physiologically acceptable level.

While direct monitoring of nitric oxide levels would be desirable, in vivo levels of nitric oxide are difficult to monitor. Since the nitrate level is related to the level of nitric oxide in the body, with increased nitric oxide levels in vivo corresponding to higher nitrate levels, to avoid the difficulties of monitoring in vivo levels of nitric oxide, it is often convenient instead to measure nitrate levels in the blood of the subject as an indicator of the nitric oxide level in a subject. In humans the physiologically compatible range of nitrate level is about 20 to about 30 $\mu$mol/liter which corresponds generally to a physiologically compatible range of nitric oxide from about 0.8 $\mu$mol/kg/hr to about 1.5 $\mu$mol/kg/hr; but those skilled in the art will appreciate that dietary intake of nitrates may substantially raise or lower the level of blood nitrates from physiological levels. However, in general, a nitrate level greater than about 50 to about 100 $\mu$mol/liter will indicate that the level of nitric oxide is above a physiologically compatible level.

A therapeutic "nitric oxide-containing gas" is one that contains a detectable concentration of nitric oxide, generally in the range from about 0.5 ppm to about 100 ppm/daily. Such nitric oxide containing gases are generally used in pediatric applications for treatment of respiratory failure. Undesirable side effects resulting from such therapeutic treatment include formation of met-hemoglobin, and the like. Nitric oxide containing gases are also used therapeutically in conjunction with nitric oxide inhalation therapy to treat patients suffering from acute lung injury, acute respiratory distress syndrome, pulmonary hypertension, and the like.

A therapeutic "nitric oxide donor" is a therapeutic agent, generally an organic or inorganic nitrate or nitrite, that releases nitric oxide in vivo. Nitric oxide donors are administered for the purpose of reducing the blood pressure of the subject and to alleviate impotence, angina, congestive heart failure, acute lung injury, acute respiratory distress syndrome, pre-ecalmpsia, and the like. The undesirable side effects associated with treatment with nitric oxide donors are manifold and include hypotension, postural hypotension, syncope, and the like. Examples of nitric oxide donors whose side effects can be reduced by the practice of the invention method include nitroglycerin, isosorbide dinitrate, sydnonimine, pirisdomine, furoxan derivatives, S-nitrosocysteine, sodium nitroprusside, FK409, S-nitrosoglutathione, amyl nitrite, and the like, as well as combinations of any two or more thereof.

A therapeutic "nitric oxide enhancer" is a therapeutic agent that does not release nitric oxide, but interferes with nitric oxide-related metabolic pathways, thereby indirectly enhancing the levels of nitric oxide in the body. Selective inhibitors of monophosphate (cGMP)-specific phosphodiesterase type 5, the enzyme that breaks down cGMP, are a category of nitric oxide enhancers used to induce smooth muscle relaxation and inflow of blood to the corpus cavernosum, resulting in penile erection. One such therapeutic agent administered in treatment of sexual dysfunction, is sildenafil citrate (Viagra®, Pfizer Corporation). Although effective for the treatment of erectile dysfunction, sildenafil citrate has undesirable side effects, such as headache, hypotension and dyspepsia, particularly when used by patients taking another nitric oxide source, such as an organic nitrate drug. Other conditions treated by nitric oxide enhancers include impotence, angina and congestive heart failure, acute respiratory distress syndrome, and the like. Additional examples of nitric oxide enhancers whose undesirable side effects can be treated by the invention method include acetylcholine, heparin, calcium ion, arginine, and the like, and combinations of two or more thereof.

A therapeutic "nitric oxide generator" is a therapeutic agent administered to generate or cause generation of nitric oxide synthase, such as a recombinantly implanted gene encoding a nitric oxide synthase, for example neuronal, endothelial or inducible nitric oxide synthase.

Still further examples of nitric oxide source(s) are those commonly administered in treatment of migraine.

In the invention method, administration of the physiologically compatible nitric oxide scavenger is timed so that the scavenger will begin to take effect an amount of time after administration of the nitric oxide source sufficient to allow the desired therapeutic effect of the source to be achieved. Therefore, the nitric oxide scavenger is either administered separately after a sufficient delay to allow the nitric oxide source to achieve the therapeutic goal, or the nitric oxide scavenger is coadministered with the nitric oxide source in a time release formulation or vehicle that substantially delays release of the nitric oxide scavenger for the amount of time necessary for the therapeutic effect of the nitric oxide source to be achieved. Those skilled in the art will appreciate that the exact time period between administration of the nitric oxide source and the nitric oxide scavenger (or substantial release of scavenger from the time release formulation), will vary depending upon such factors as the condition being treated by the nitric oxide source, the type of nitric oxide source administered (e.g., the effect of a nitric oxide containing gas is instantaneous), the age, weight, and general health of the subject, the amount of the nitric oxide source administered, and the like. However, in general, the nitric oxide scavenger is administered or substantial release from the time release formulation is delayed for a period from about 1 minute to about several weeks after administration of the nitric oxide source, for example, from about 1 minute to about 5 hours, or from about 1 minute to about 2 hours.

As readily recognized by those of skill in the art, a variety of agents can be used as nitric oxide scavengers. Examples of physiologically compatible nitric oxide scavengers include non-heme iron-containing peptides or proteins, porphyrins, metalloporphyrins, dithiocarbamates, dimercaptosuccinic acid, phenanthroline, desferrioxamine, pyridoxal isonicotinoyl hydrazone (PIH), 1,2-dimethyl-3-hydroxypyrid-4-one (L1), [+] 1,2-bis(3,5-dioxopiperazine-1-yl)propane (ICRF-187), 2-mercaptonicotinic acid, nitronyl nitroxide, nitric oxide chelotropes (e.g., compounds containing the 7,7,8,8-tetraalkyl-O-quinodimethane type moiety), 2-phenyl-4,4,5,5-tetramethylimidazoline-1-oxyl 3-oxide (PTIO), carboxy-PTIO, phenyl-n-tert-butyl nitrone, as well as other nitrone derivatives, and the like. A presently preferred class of compounds useful for such purpose is the dithiocarbamates. Dithiocarbamate-containing nitric oxide scavengers contemplated for use in the practice of the present invention include any physiologically compatible derivative of the dithiocarbamate moiety (i.e., $(R)_2N$—C (S)—SH). Such compounds can be described with reference to the following generic structure (I):

$$[R_1R_2N-C(S)-S^-]_xM^{+1,+2,+3} \qquad (I)$$

wherein:
  each $R_1$ and $R_2$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, substituted acyl, or $R_1$ and $R_2$ can cooperate to form a 5-, 6- or 7-membered ring including N, $R_1$ and $R_2$, or $R_1$ or $R_2$ is a divalent moiety selected from the group consisting of alkylene, substituted alkylene, oxyalkylene, substituted oxyalkylene, alkenylene, substituted alkenylene, arylene, substituted arylene, alkarylene, substituted alkarylene, aralkylene and substituted aralkylene, wherein said divalent moiety serves as the same substituent for two dithiocarbamate structures, thereby linking said structures together so as to form a bis(dithiocarbamate) species, x is 1 or 2, M is optional, and, when present, is a monovalent cation when x is 1, or M is a physiologically compatible divalent or trivalent transition metal cation when x is 2, and when M is not present, x is 2 and the dithiocarbamate is a disulfide dimer.

Among the presently preferred compounds having the above-described generic structure (I) are those wherein:
  each of $R_1$ and $R_2$=a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl, and $M=Fe^{+2}$ or $Fe^{+3}$.

and those having the above-described generic structure wherein:
  $R_1$=a $C_2$ up to $C_8$ alkyl or substituted alkyl, wherein the substituents are selected from carboxyl, acetyl, pyridinyl, pyrrolidinyl, amino, amido, hydroxy or nitro, $R_2$ is selected from a $C_1$ up to $C_6$ alkyl or substituted alkyl, or $R_2$ can cooperate with $R_1$ to form a 5-, 6- or 7-membered ring including N, $R_2$ and $R_1$ and $M=Fe^{+2}$.

Additional presently preferred compounds having the above-described generic structure are those wherein:
  $R_1$=a $C_2$ up to $C_8$ alkyl or substituted alkyl, wherein the substituents are selected from carboxyl, acetyl, amido or hydroxy, $R_2$=a $C_1$ up to $C_4$ alkyl or substituted alkyl, and $M=Fe^{+2}$.

When $R_1$ and $R_2$ cooperate to form a 5-, 6- or 7-membered ring, the combination of $R_1$ and $R_2$ can be a variety of saturated or unsaturated 4, 5 or 6 atom bridging species selected from alkylene, alkenylene or —O—, —S—, —C(O)— and/or —N(R)— containing alkylene moieties, wherein R is hydrogen or a lower alkyl moiety.

Monovalent cations contemplated for incorporation into compounds of structure (I) include $H^+$, $Na^+$, $NH_4^+$, tetraalkyl ammonium, and the like. Physiologically compatible divalent or trivalent transition metal cations contemplated for incorporation into the above compounds include charged forms of iron, cobalt, copper, manganese, ruthenium, or the like (e.g., $Fe^{+2}$, $Fe^{+3}$, $Co^{+2}$, $Co^{+3}$, $Cu^{+2}$, $Mn^{+2}$, $Mn^{+3}$ or $Ru^{+3}$). In accordance with the present invention, the ratio of dithiocarbamate-species to counter-ion M can vary widely. Thus, dithiocarbamate-containing nitric oxide scavenger can be administered without any added metallic counter-ion (i.e., $M=H^+$, or a transition metal cation to dithiocarbamate-species ratio of zero), with ratios of transition metal cation to dithiocarbamate-species up to about 1:2 (i.e., a 2:1 dithiocarbamate:transition metal cation complex) being suitable.

The dithiocarbamates presently most preferred for use in the practice of the present invention are suitable for oral administration, i.e., are stable at the pH in the stomach. For example the disulfide dimer of Structure I (wherein M is absent and x=2) resists acid lability down to pH of about 1 but releases the active monomers under the reducing conditions found in the lower alimentary tract. The presently preferred dithiocarbamates are also substantially hydrophilic, thereby facilitating administration and transport, e.g., in the bloodstream, as well as in the interstitial space. This is in contrast to dithiocarbamates employed in the past, which are generally hydrophobic, in order to facilitate transport across cell membranes, etc., an activity which is not required of dithiocarbamates employed for reduction of unacceptably high nitric oxide levels.

As employed herein, "substituted alkyl" comprises alkyl groups further bearing one or more substituents selected from hydroxy, alkoxy (of a lower alkyl group; wherein a lower alkyl group has about 1–4 carbon atoms), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "alkenyl" refers to straight or branched chain hydrocarbyl groups having at least one carbon-carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "aroyl" refers to aryl-carbonyl species such as benzoyl and "substituted aroyl" refers to aroyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "acyl" refers to alkyl-carbonyl species.

As employed herein, "halogen" refers to fluoride, chloride, bromide or iodide atoms.

The term "effective amount" as applied to a nitric oxide source according to the invention means the quantity necessary to treat, cure or alleviate the symptoms of the intended disease state. The term "effective amount" as applied to a nitric oxide scavenger according to the invention means the amount necessary to prevent, to cure, or at least partially arrest one or more side effects in a subject caused by therapeutic administration of the nitric oxide source, for example, elevated nitric oxide, elevated nitrate level, hypotension, postural hypotension, syncope, headache, and the like. A subject is any mammal, preferably a human. Amounts effective for substantially counteracting the side effects of a nitric oxide source will, of course, depend on the severity of the side effects, the amount of the nitric oxide source administered, and the weight and general state of the subject. Typically, animal models may be used to determine suitable dosages to be used to achieve a reduction in such side effects. In addition, various general considerations taken into account in determining the "effective amount" are known to those of skill in the art and are described, e.g., in Gilman et al., eds., *Goodman And Gilman's: The Pharmacological Bases of Therapeutics,* 8th ed., Pergamon Press, 1990; and *Remington's Pharmaceutical Sciences,* 17th ed., Mack Publishing Co., Easton, Pa., 1990, each of which is herein incorporated by reference.

Since individual subjects may present a wide variation in severity of symptoms and each nitric oxide source and nitric oxide scavenger drug has its unique therapeutic characteristics, the precise mode of administration, dosage employed and treatment protocol for each subject is left to the discretion of the practitioner.

In accordance with another embodiment of the present invention, there are provided formulations comprising an effective amount of a biologically compatible nitric oxide source as described herein, and an effective amount of a physiologically compatible nitric oxide scavenger (e.g., a compound having the structure I, as described above) in a time release delivery vehicle that substantially delays release of the scavenger for a sufficient amount of time after administration of the formulation to a subject in need thereof that the nitric oxide source achieves a beneficial effect prior to the release of the scavenger. In one embodiment, the time release delivery vehicle is selected to substantially delay release of the scavenger for about 30 minutes to about 48 hours after administration of the formulation to the subject.

The formulations and methods of the invention are particularly suited to reducing side effects induced by simultaneous administration to a subject with cardiovascular problems of a nitrate or nitrite, such as nitroglycerin, and a nitric oxide enhancer, such as sildenafil citrate, which is sold under the brand name of Viagra® by (Pfizer Laboratories). Since the combination of drugs has been lethal to several subjects, the recommended method of administration is by coingestion of nitric oxide enhancer (i.e., Viagra®) and the nitric oxide scavenger with the latter being in a time release formulation designed to accomplish substantial release of the scavenger from about 30 minutes to about 48 hours, preferably, about 30 minutes to about 2 hours, following the coingestion of the two.

In another aspect, the invention provides a kit comprising a unit dose of a nitric oxide source as described herein in a pharmaceutically acceptable carrier therefor, and a unit dose of a physiologically compatible nitric oxide scavenger (e.g., a compound having the structure I, as described above) in a pharmaceutically acceptable carrier therefor, optionally contained within a time release vehicle. After substantial release of the nitric oxide scavenger from the time release vehicle has been delayed for the appropriate desired time, the rate of release of the scavenger from the time release vehicle is generally in the range from about 0.01 mmoles/kg body weight of the subject/hour up to about 1.0 mmoles/kg/hr.

Those skilled in the art will understand that the delay before substantial release of the nitric oxide scavenger from the time release vehicle in the kit is selected to be any appropriate time period, depending upon the factors generally taken into consideration in determining the period of time necessary for the nitric oxide source to achieve its therapeutic goal. In general, however, the time release vehicle is formulated to delay release of the scavenger for about 1 minute to about 2 to about 5 hours.

The term "unit dose," when used in reference to a "nitric oxide source" or "nitric oxide scavenger" herein, refers to a quantity thereof suitable as unitary dosage for the subject, each unit containing a predetermined quantity of active material calculated to produce the desired therapeutic effect in association with the required pharmaceutically acceptable carrier and/or vehicle therefor. Generally the unit dose of a particular nitric oxide scavenger is determined with respect to the unit dose of the particular nitric oxide source whose effects are sought to be counteracted at the appropriate time. For example, in humans, N-methyl-D-glucamine (MGD) or other dithiocarbamate is administered orally at a dose of from about 10 to about 20 mg/kg about 30 to about 120 min after the patient has taken a dose of Viagra® of about 25 mg/kg to about 20 mg/kg, as illustrated in Example 2 herein.

In one embodiment, the kit is packaged in the form of a bubble pack having paired bubbles for the nitric oxide source and the nitric oxide scavenger arranged on a pairwise basis, with one pair for each administration. The term "bubble pack" refers to packaging devices wherein unit doses are displayed and/or contained within separate subcompartments (often having a see-through membrane on one side fused to an opposing burstable membrane on the opposite side with the unit dosages positioned pairwise between the two membranes) and wherein the unit dose is removed from its separate subcompartment for administration by breaking open the subcompartment containing the unit dose, for example by bursting the separately containing membrane).

Such kits afford the advantage that the person who removes a unit dose from the bubble pack can readily determine how many unit dosages in the bubble pack have been removed and whether both members of any given pair have been removed for administration. It is contemplated within the scope of the invention that the pairwise subcompartments can be labeled with an indication of an appropriate dosage pattern, for example, by days of the week if the unit dosage of the nitric oxide source and corresponding unit dose of the nitric oxide scavenger are to be each administered on a daily basis. It is presently preferred that both the nitric oxide source and the nitric oxide scavenger in the kit be formulated for oral administration.

Since individual subjects may present a wide variation in severity of symptoms and each active ingredient has its unique therapeutic characteristics, it is up to the practitioner to determine a subject's response to treatment and vary the unit dosages accordingly.

The nitric oxide source and the nitric oxide scavenger in the invention formulations and/or kits can be independently contained within a suitable vehicle rendering said formulation amenable to oral delivery, transdermal delivery, intravenous delivery, intramuscular delivery, topical delivery, nasal delivery, and the like.

Depending on the mode of delivery employed, the above-described formulations can be delivered in a variety of pharmaceutically acceptable forms. For example, the above-described formulations can be delivered in the form of a solid, solution, emulsion, dispersion, micelle, liposome, and the like.

Pharmaceutical formulations of the present invention can be used in the form of a solid, a solution, an emulsion, a dispersion, a micelle, a liposome, and the like, wherein the resulting formulation contains one or more of each of the nitric oxide scavenging and therapeutically active compounds contemplated for use in the practice of the present invention, as active ingredients thereof, in admixture with an organic or inorganic carrier or excipient suitable for enteral or parenteral applications. The active ingredients may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compounds (i.e., "therapeutic agents" and nitric oxide scavenging compounds (e.g., compounds of structure I as described herein)) are included in the pharmaceutical formulation in an amount sufficient to produce the desired effect upon the target process, condition or disease.

Pharmaceutical formulations containing the active ingredients contemplated herein may be in a form suitable for oral use, for example, as tablets, troches, lozenges, aqueous or oily suspensions, dispersible powders or granules, emulsions, hard or soft capsules, or syrups or elixirs. Formulations intended for oral use may be prepared according to any method known in the art for the manufacture of pharmaceutical formulations. In addition, such formulations may contain one or more agents selected from a sweetening agent (such as sucrose, lactose, or saccharin), flavoring agents (such as peppermint, oil of wintergreen or cherry), coloring agents and preserving agents, and the like, in order to provide pharmaceutically elegant and palatable preparations. Tablets containing the active ingredients in admixture with non-toxic pharmaceutically acceptable excipients may also be manufactured by known methods. The excipients used may be, for example, (1) inert diluents such as calcium carbonate, lactose, calcium phosphate, sodium phosphate, and the like; (2) granulating and disintegrating agents such as corn starch, potato starch, alginic acid, and the like; (3) binding agents such as gum tragacanth, corn starch, gelatin, acacia, and the like; and (4) lubricating agents such as magnesium stearate, stearic acid, talc, and the like. The tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredients are mixed with an inert solid diluent, for example, calcium carbonate, calcium phosphate, kaolin, or the like. They may also be in the form of soft gelatin capsules wherein the active ingredients are mixed with water or an oil medium, for example, peanut oil, liquid paraffin, or olive oil.

The pharmaceutical formulations may also be in the form of a sterile injectable solution or suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, or synthetic fatty vehicles, like ethyl oleate, or the like. Buffers, preservatives, antioxidants, and the like, can be incorporated as required.

Formulations contemplated for use in the practice of the present invention may also be administered in the form of suppositories for rectal administration of the active ingredients. These formulations may be prepared by mixing the active ingredients with a suitable non-irritating excipient, such as cocoa butter, synthetic glyceride esters of polyethylene glycols (which are solid at ordinary temperatures, but liquify and/or dissolve in the rectal cavity to release the active ingredients), and the like.

The invention will now be described in greater detail by reference to the following non-limiting examples.

EXAMPLE 1

Effect of Intravenous Infusion of MGD or MGD-Fe Complex into the Blood Circulation 1A. N-Methyl-D-glucamine and carbon disulfide were obtained from Aldrich (Milwaukee, Wis.). N-Methyl-D-glucamine dithiocarbamate (MGD) was synthesized by following the method of Shinobu et al. (*Acta Pharmacol. Toxicol.* 54:189–194 (1984)). MGD was infused intravenously into rats via a cannulated femoral vein at a dose of 30–600 mg/kg and the effects of MGD treatment on the mean arterial pressure of rats was measured by a physiological recorder (Grass Instrument) via a cannulated femoral artery. Control rats were infused with saline alone. During the three hour observation period, the mean arterial pressure remained about 100 mm Hg in both the test and control groups of animals.

1B. As described previously (see Lai and Komarov in *FEBS Lett.* 345:120–124 (1994)), one [(MGD)$_2$/Fe] complex (MGD-Fe) binds to one molecule of nitric oxide to form a [(MGD)$_2$/Fe—NO] complex. Whereas free nitric oxide is a potent vasodilator, nitric oxide bound to MGD-Fe is not. The resulting complex is then excreted from the body in the urine, thereby reducing in vivo nitric oxide levels.

To test the effect of MGD-Fe on the mean arterial pressure of healthy rats, an experiment similar to that of Section 1A was conducted, except that the nitric oxide scavenger MGD-Fe was injected at a dose of 30–200 mg/kg. The results were the same as those obtained in Section 1A when MGD was administered. These results suggest that the administration of MGD or MGD-Fe complex exerts no effects on the normal blood pressure of healthy rats.

1C. Oral Administration of L-proline Dithiocarbamate (L-PD) Does Not Cause Hypertension or Tachycardia A pressure sensor chip for a telemetric device (Data Scientific International, Saint Paul, Minn.) was implanted in the dorsal abdominal aorta of male Wistar rat (250–280 g). The rats were allowed to recover from the surgery over a period of 24 hours. The implanted rats were separated into two groups (n=3); One received 10 mg/ml of L-proline dithiocarbamate (L-PD) in drinking water and the other received only distilled water for 14 days. There was no significant difference in the amounts of water consumption and weight gain between the experimental and control groups during the course of the study. On average, in the experimental group, each rat received about 800 mg/kg/day for 14 days.

Figure 1B:
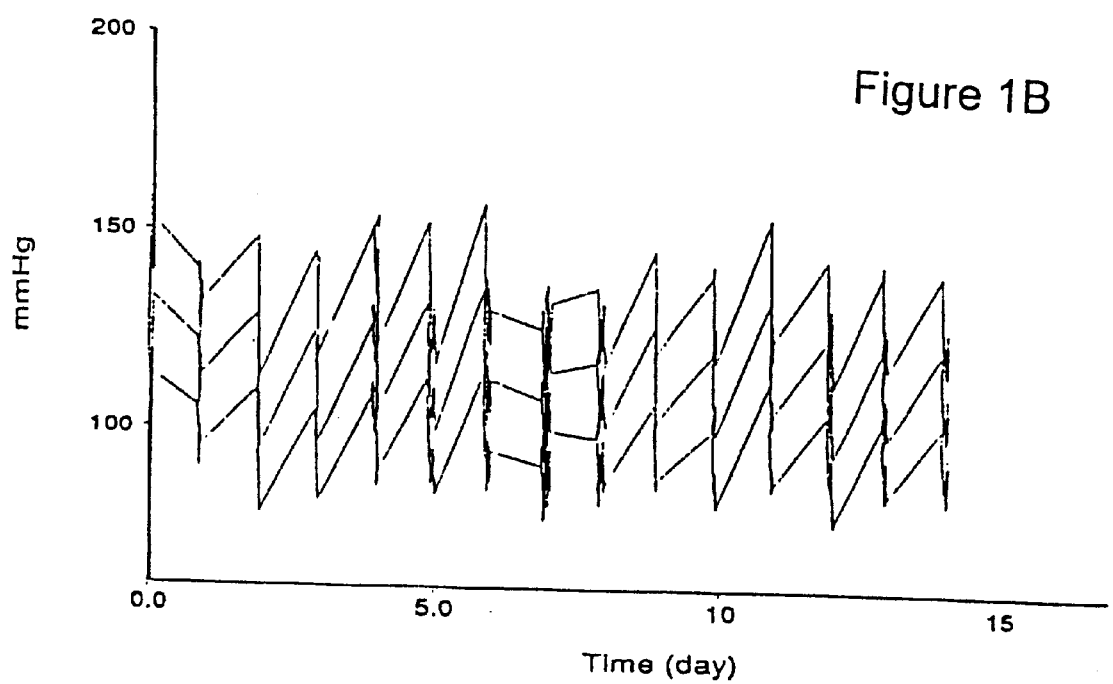
FIG. 1B is a graph showing the blood pressure (mm Hg) of rats orally administered 10 mg/ml of L-proline dithiocarbamate in drinking water over a time course of 14 days. The middle line of the graph represents the mean arterial blood pressure, the top line of the graph represents the systolic blood pressure, and the bottom line represents the diasystolic blood pressure.

The heart rate and blood pressure of the sensor-implanted rats were measured non-invasively daily using a telemetric device (Data Scientific International) Both heart rate and blood pressure in the experimental group as shown in FIGS. 1A and 1B, respectively, were identical to those of the controls (not shown). The data in FIG. 1 showed that the oral administration of L-PD for 14 days has no effect on either heart rate or blood pressure in rats having physiological levels of nitric oxide.

EXAMPLE 2

Administration of a Nitric Oxide Scavenger Reduces Hypotensive Side Effects Caused by Viagra® in Impotent Subjects N-methyl-D-glucamine (MGD) or other dithiocarbamate at a dose of 10–20 mg/kg is given orally 30–120 min after the subject has ingested 25, 50 or 100 mg of oral sildenafil citrate (Viagra®). MGD, which chelates ferrous ions from the intestine to form the MGD-Fe complex, is absorbed and distributed into the blood circulation, where it binds excessive nitric oxide generated due to the administration of the nitric oxide source sildenafil citrate, thereby forming MGD-Fe—NO complex. Whereas the free nitric oxide is a potent vasodilator, the nitric oxide bound to the MGD-Fe complex forming MGD-Fe—NO is not active. The complex then is excreted from the kidneys into the urine. Removal of excessive nitric oxide in the circulation, therefore, reduces the hypotensive effect caused by Viagra®.

EXAMPLE 3

Administration of NO Scavenger Reduces Hypotensive Side Effects Caused by Combination Effects of Nitroglycerin and Viagra® in Angina Patients Nitroglycerin is a nitric oxide donor. When taken sublingually (0.3–0.6 mg) or by spray, it is effective in reducing arteriolar and venous tone and lowers the oxygen demand of the heart. Viagra® is a nitric oxide enhancer effective in the treatment of impotence. The combination of nitroglycerin, or other organic nitrates, and Viagra® can cause life-threatening extreme hypotension, and even death.

N-methyl-D-glucamine (MGD) disulfide or other dithiocarbamate at a dose of 10–20 mg/kg is given to patients taking both nitroglycerin and Viagra® to remove excessive nitric oxide in the blood circulation and to prevent hypotensive episodes.

While the invention has been described in detail with reference to certain preferred embodiments thereof, it will be understood that modifications and variations are within the spirit and scope of that which is described and claimed.

That which is claimed is:

1. A formulation comprising:
   an effective amount of a biologically compatible nitric oxide source, and
   an effective amount of a compound that releases a physiologically compatible nitric oxide scavenger when activated in a time, release delivery vehicle that substantially delays release of the scavenger for a sufficient amount of time after administration of the formulation to a subject in need thereof that the nitric oxide source achieves a beneficial effect prior to the release of the scavenger.

2. The formulation according to claim 1, wherein the compound that releases a physiologically compatible nitric oxide scavenger when activated has the structure as follows:

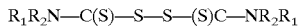

$$R_1R_2N—C(S)—S—S—(S)C—NR_2R_1$$

wherein:
   each of $R_1$ and $R_2$ is independently selected from a $C_1$ up to a $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, hereroaryl, substituted heteroaryl, alkyleryl, substituted alkylaryl, arylalkyl, substituted arylalkyl, or
   $R_1$ and $R_2$ can cooperate to form a 5-, 6-, or 7-membered ring including N, $R_1$, and $R_2$, or
   $R_1$ and $R_2$ is a divalent moiety selected from the group consisting of alkylene, substituted alkylene, oxyalkylene, substituted oxyalkylene, alkenylene, substituted alkenylene, arylene, substituted arylene, alkarylene, substituted alkarylene, aralkylene and substituted aralkylene, wherein said divalent moiety serves as the same substituent for two disulfide dithiocarbamate structures, thereby linking said structures together so as to form a bis(dithiocarbamate).

3. The formulation according to claim 2 wherein:
   each of $R_1$ and $R_2$ is independently selected from a $C_1$ up to $C_{12}$ alkyl, a substituted alkyl, an alkenyl, a substituted alkenyl, an alkynyl end a substituted alkynyl, wherein the substituents are selected from the group consisting of carboxyl, —C(O)H, oxyacyl, phenol, phenoxy, pyridinyl, pyrrolidinyl, amino, amido, hydroxy, nitro and sulfuryl.

4. The formulation according to claim 2 wherein:
   $R_1$ is selected from a $C_2$ up to $C_8$ unsubstituted alkyl, and an alkyl having a substitutent selected from the group consisting of carboxyl, acetyl, pyridinyl, pyrrolidinyl, amino, amido, hydroxy and nitro substituents, and
   $R_2$ is selected from a $C_1$ up to $C_6$ unsubstituted or substituted alkyl, or $R_2$ can cooperate with $R_1$ to form a 5-, 6- or 7-membered ring including N, $R_2$ and $R_1$.

5. The formulation according to claim 2 wherein;
   $R_1$ is independently selected from a $C_2$ up to $C_8$ alkyl, and an alkyl having a substituent selected from the group consisting of a carboxyl, acetyl, amido and hydroxy substituents, and
   $R_2$ is independently selected from a $C_1$ up to $C_4$ alkyl or substituted alkyl.

6. The formulation according to claim 2 wherein $R_1$ and $R_2$ cooperate to form a 5-, 6- or 7-membered ring, and the combination of $R_1$ and $R_2$ is a saturated or unsaturated 4, 5 or 6 atom bridging species selected from the group consisting of alkylene, alkenylene, —O—, —S—, —C(O)— and —N(R)— containing alkylene moieties, wherein R is hydrogen or a lower alkyl moiety.

7. The formulation according to claim 2 wherein:
   each of $R_1$ and $R_2$ is independently selected from a $C_1$ up to $C_{12}$ alkyl, a substituted alkyl, an alkenyl, a substituted alkenyl, an alkynyl and a substituted alkynyl, wherein the substituents are selected from the group consisting of carboxyl, —C(O)H, oxyacyl, phenol, phenoxy, pyridinyl, pyrrolidinyl, amino, amido, hydroxy, nitro and sulfuryl.

8. The formulation according to claim 2 wherein:
   $R_1$ is selected from a $C_2$ up to $C_8$ unsubstituted alkyl, and an alkyl having a substitutent selected from the group consisting of carboxyl, acetyl, pyridinyl, pyrrolidinyl, amino, amido, hydroxy and nitro substituents, and
   $R_2$ is selected from a $C_1$ up to $C_6$ unsubstituted or substituted alkyl, or $R_2$ can cooperate with $R_1$ to form a 5-, 6- or 7-membered ring including N, $R_2$ and $R_1$.

9. The formulation according to claim 2 wherein:
   $R_1$ is independently selected from a $C_2$ up to $C_8$ alkyl, and an alkyl having a substituent selected from the group consisting of a carboxyl, acetyl, amido and hydroxy substituents, and
   $R_2$ is independently selected from a $C_1$ up to $C_4$ alkyl or substituted alkyl.

10. The formulation according to claim 2 wherein $R_1$ and $R_2$ cooperate to form a 5-, 6- or 7-membered ring, and the combination of $R_1$ and $R_2$ is a saturated or unsaturated 4, 5 or 6 atom bridging species selected from the group consisting of alkylene, alkenylene, —O—, —S—, —C(O)— and —N(R)— containing alkylene moieties, wherein R is hydrogen or a lower alkyl moiety.

11. A kit comprising
   a unit dose of a nitric oxide source in a pharmaceutically acceptable carrier therefor, and
   a unit dose of a compound that releases a physiologically compatible nitric oxide scavenger when activated in a pharmaceutically acceptable carrier therefor, optionally contained within a time release vehicle.

12. The kit according to claim 11 wherein the kit is in the form of a bubble pack with paired bubbles for the nitric oxide source and the compound that releases a nitric oxide scavenger when activated arranged on a pairwise basis, with one pair for each administration.

13. The kit according to claim 11 wherein the nitric oxide source and the compound that releases a nitric oxide scavenger when activated are formulated for oral administration.

* * * * *